United States Patent [19]

Strade

[11] 4,049,805
[45] * Sept. 20, 1977

[54] STEROIDAL ERYTHROPOIETIC AGENTS AND THERAPEUTIC COMPOSITIONS AND METHODS

[75] Inventor: Henry A. Strade, Montville, N.J.

[73] Assignee: Akzona Incorporated, Asheville, N.C.

[*] Notice: The portion of the term of this patent subsequent to Jan. 18, 1994, has been disclaimed.

[21] Appl. No.: 693,249

[22] Filed: June 4, 1976

Related U.S. Application Data

[63] Continuation-in-part of Ser. No. 618,176, Sept. 30, 1975, Pat. No. 4,004,005.

[51] Int. Cl.$^2$ .......................................... A61K 31/565
[52] U.S. Cl. .................................................. 424/243
[58] Field of Search ........................................ 424/243

[56] References Cited
PUBLICATIONS

Chem. Abst. vol. 82, General Subject Index (1975) p. 602GS.

*Primary Examiner*—Sam Rosen
*Attorney, Agent, or Firm*—Francis W. Young

[57] ABSTRACT

The stimulation of erythropoiesis in humans and other warm-blooded animals is produced by administration of an effective amount of a compound selected from the group consisting of 3α-hydroxy-5β-estrane-17-one, 3β-hydroxy-5β-estrane-17-one, and the 3 esters and 3 ethers thereof. The steroids are particularly advantageous in that they exhibit an unexpected low level of pyrogenicity as compared to etiocholanolone, a known pyrogen.

7 Claims, No Drawings

STEROIDAL ERYTHROPOIETIC AGENTS AND THERAPEUTIC COMPOSITIONS AND METHODS

CROSS-REFERENCE TO RELATED APPLICATION

This application is a continuation-in-part of application Ser. No. 618,176, filed Sept. 30, 1975, now U.S. Pat. No. 4,004,005.

BACKGROUND OF THE INVENTION

This invention relates to novel non-pyrogenic steroidal erythropoietic agents, and to therapeutic compositions containing the same and methods of treatment. More particularly, the invention concerns 3α-hydroxy-5β-estrane-17-one (19 nor-etiocholanolone), and 3β-hydroxy-5β-estrane-17-one, and 3-substituted derivatives thereof, and their application in the stimulation of erythropoiesis.

Erythropoiesis is the process of formation of red blood cells.

The term anemia implies an abnormally low number of circulating red cells or a decreased concentration of hemoglobin in the blood. The appearance of anemia reflects either marrow failure or excessive red cell loss, or both. Marrow failure, i.e., reduced erythropoiesis, may occur as a result of a nutritional deficiency, toxic exposure, tumor invasion, or other and sometimes unknown causes.

For the treatment of anemias of bone marrow failure (hypoplastic and aplastic anemias), it has been proposed to use substances which might stimulate the marrow, such as androgens or corticosteroids. Campbell et al. U.S. Pat No. 3,383,282 discloses various 3,5-androstadiene-3,17-diol derivatives as possessing erythropoietic activity. Schmidlin et al. U.S. Pat. Nos. 3,519,659 and 3,519,660 disclose various prednisolone derivatives having antileukemia activity.

It is known that erythropoietic activity is exhibited by metabolites of certain androgenic, anabolic, or progestational steroids. Thus, Levere et al. Proceedings of a Symposium held in conjunction with the American Society of Hematology, Dec. 4, 1971, Chapter III, discloses that etiocholanolone, a human metabolite of testosterone, possesses erythropoietic activity. Jepson, ibid., Chapter II, disclosed that nandrolone (19-nortestosterone; 17-β-hydroxy-19-nor-4-androsten-3-one), an anabolic steroid, possesses erythropoietic activity similar to testosterone. This substance, however, has the drawback of exhibiting androgenic side-effects. It is known in the form of its decanoate, described in DeWitt et al U.S. Pat. No. 2,998,423. Etoicholanolone possesses the substantial drawback of being a pyrogen in man.

GENERAL DESCRIPTION OF THE INVENTION

In accordance with the present invention, it has been found that certain estrane derivatives which contain the 5β-H configuration exhibit erythropoietic activity, while at the same time they are nonpyrogenic and exhibit little or no androgenic side effects.

The conpounds found to be non-pyrogenic and active in stimulating erythropoiesisare 3α-hydroxy-5β-estrane-17-one (19-norethiocholanolone and its 3-esters and 3-ethers, and 3β-hydroxy-5β-estrane-17-one, and its 3-esters and 3-ethers.

19-noretiocholanolone is a known compound and is disclosed by Engel et al, J. Biol. Chem. 231, 1, 159 (1958). This compound is also disclosed in an article by Counsell in Tetrahedron, Vol.15, 202–211 (1961). 19-noretiocholanolone may also be synthesized by hydrogenating nandrolone 17-acetate to the corresponding $5_H$-3keto-17β-acetate by the method described in J. Org. Chem. 31. 2394 (1966), then hydrogenating the 3-keto group to form the 3α-hydroxy group using lithiumaluminum tri-tert-butoxyhydride, protecting the 3α-hydroxy group and hydrolyzing the 17β-acetate to 17-keto with $CrO_3$-pyridine, and finally removing the 3α-protecting group.

3β-Hydroxy-5β-estrane-17-one is a known compound and is disclosed, together with a method for its preparation, in the aforesaid article by Counsell in Tetrahedron, Vol. 15, 202–211 (1961), at page 204, namely the reduction of 5β-estrane-3,17-dione with Raney nickel in ethanol.

The 3-esters of the aforementioned compounds which exhibit erythropoietic activity include those of pharmaceutically acceptable acids, which may be either inorganic or organic. Examples of inorganic acids include hydrochloric, sulfuric, and phosphoric, while saturated or unsaturated organic carboxylic acids having 3 to 18 carbon atoms may also be employed. The preparation of these esters can be carried out in conventional manner by reacting the 3α-hydroxy or 3β-hydroxy steroid with the acid, or with its corresponding anhydride or acyl halide.

As examples or organic carboxylic acids, there may be employed aliphatic mono- or polycarboxylic acids, such as propionic, butyric, valeric, capric, decanoic, undecanoic lauric, tridecylic, pyristic, oleic, palmitic, stearic, trimethylacetic, diethyl acetic, undecylenic, malonic, succinic, glutaric, pimelic, and tartaric acids. There may also be employed cycloaliphatic carboxylic acids, such as cyclohexane carboxylic, cyclopentylpropionic, and cyclohexylbutyric acids, and also araliphatic carboxylic acids, such as phenylacetic, phenylpropionic, and phenyl butyric acids, and also aromatic acids, such as benzoic acid.

The 3α-hydroxy or 3β-hydroxy steroid may be etherified with a group derived from an aliphatic, aromatic, araliphatic, or heterocyclic hydrocarbon. Examples of suitable ether groups include methoxy, ethoxy, propoxy, benxyloxy, and phenylethoxy.

The presently preferred erythropoietic agents according to the invention are 19-noretiocholanolone and its 3-decanoate ester, and 3β-hydroxy-5β-estrane-17-one- and its 3-decanoate ester.

DESCRIPTION OF THE PREFERRED EMBODIMENT

The following examples illustate the therapeutic compositions of the invention and their application, but are not to be regarded as limiting:

EXAMPLE 1

Erythropoietin Bioassay 19-noretiocholanolone was administered to mice as a single subcutaneous injection of 2.5 mg. in a 2-propanediol vehicle, at various intervals following induced hypoxia. The first injection was made on the third day post-hypoxia; on the fifth post-hypoxic day, 0.5 $\mu Ci^{59}FeCl_3$ was injected intravenously; the percent $^{59}Fe$-incorporation into the red cells was determined on day 7 post-hypoxia. The 19-noretiocholanolone stimulated radioiron incorporation significantly, the figure for % RBC-$^{59}$Fe incorporation being $5.82 \pm 1.21$ ($p < 0.05$).

EXAMPLE 2

Rat Marrow Bioassay 19-noretiocholanolone was added in 1 μ 1 of 2-propanediol to rat bone marrow, (S-D ♂ ♂ , ~ 100 – 150 g.) at the initiation of the cultures; about 72 hours later 0.5 Ci$^{59}$Fe, bound to transferrin, was added to the cultures; radioheme was extracted 6 hours later and quantitated. The data suggest that 19-noretiocholanolone is active in this system:

| Concentration (M) | $3 \times 10^{-7}$ | $3 \times 10^{-8}$ | $3 \times 10^{-9}$ | $3 \times 10^{-10}$ |
|---|---|---|---|---|
| | 54 | 46 | 172 | $180 \pm 47.9$ |

EXAMPLE 3

$^{14}$C-Labeled Hemoglobin

Human marrow cultures were treated with 19-noretiocholanolone for three days; 3 μ of $^{14}$C-valine was added for the last 24 of culture. Hemoglobin was isolated simultaneously from cells cultured with either 2-propanediol or the steroid ($3 \times 10^{-10}$M). The specific activity ($^{14}$C-cpm/$A_{540}$) of each was calculated and the ratio determined. The data show that the steroid was stimulatory:

| | $^{14}$C-hemoglobin[1] |
|---|---|
| 19-noretiocholanolone | 1.34 |

[1] ratio of the specific activity of a steroid-treated culture to a 2-propanediol-treated culture.

EXAMPLE 4

Human Marrow Cultures

Radioiron incorporation into heme was determined in the same manner as in the rat marrow cultures of Example 2. The 19-noretiocholanolone was evaluated at a concentration of $3 \times 10^{-8}$M except in the marrow obtained from a patient with no demonstrable disease where a concentration of $5 \times 10^{-10}$M as used. The test data are as follows:

| % Fe-Heme Incorporation | | | | |
|---|---|---|---|---|
| No Demonstrable Disease | Systemic Lupus Erythematosus | Mycosis Fungoides | Hemolytic Anemia | Rhabdomyosarcoma |
| 90[1] | 144 | 148 | 93 | 105 |

[1] The vehicle is considered as 100%.

The foregoing data indicate that 19-noretiocholanolone stimulates erythropoiesis both in vivo and in vitro.

The foregoing compounds are adapted for the administration thereof to humans and other warm-blooded animals in amounts effective to stimulate erythropoiesis, such amounts being generally in the range from about 5 to about 500 mg. per unit dosage. The usual method of administration is parenterally, for which purpose the compound may be prepared in a form suitable for injection as a solution or suspension in m ml. ampoules. The following is an example of such a preparation.

EXAMPLE 5

Ampoule Dosage Form

The dosage form can be prepared by admixing 500 g. of 19-noretiocholanolone or its 3-esters or ethers into 2 liters of sterile sesame oil containing about 500 ml. of benzyl alcohol as a preservative, and heating the resulting mixture to about 80° C. to obtain a solution. The solution is allowed to return to room temperature and the volume is increased to 10 liters by addition of sesame oil. The solution is filtered through a bacteriological membrane filter and is packaged into dosage forms, e.g., vials of 2 or 5 ml or ampoules of 1 ml. The strength of the steroid solution is about 50 mg./cc.

EXAMPLE 6

Erythropoietic Activity of 3β-hydroxy-5β-estrane-17-one- and Its 3-Decanoate

It is known that certain steroids are porphyrogenic, i.e. they induce porphyrin synthesis and induce heme formation in cells. The test system used in investigations of this activity is the primary avian lever cell culture system described by Granick and Kappas, J. Boil. Chem. 242, 4587–93 (1967). In accordance with this technique, livers of 16 to 17 day old chick embroyos are minced, and the cells separated by trypsin. Suspensions containing 3 to $5 \times 10^5$ cells are inoculated into vials which contain a cover slip and 1.0 ml. of Eagle's basal medium supplemented with glutamine, fetal bovine serum, and antibiotics. The vials are incubated at 37° C in 5% $CO_2$ and air for 24 hours. The medium is then replaced, and the addition of the steroid is made as required. Following reincubation for an additional 20 to 22 hours, the cover slips, now overgrown with a monolayer of hepatic parenchymal cells, are examined under phase and flourescence optics. Semi-quantitative estimates of cellular porphyrins are made on the basis that values of fluorescence intensity ranging from +1.0 to +4.0 are equivalent to approximately 5 to $50 \times 10^{-11}$ moles of protoporphyrin per mg. of protein on the cover slip.

The above steroid and its 3-ester were tested for induction of porphyrin synthesis using the foregoing technique, in cultured chick embryo liver cells. The cells were grown for 20 hours in tissue culture. At the end of the 20th hour, the growth medium was replaced with fresh medium, and the compounds were added. Cells were incubated for another 20 hours and porphyrins and protein concentration were determined at the end of incubation. The amounts of protoporphyrin formed reflect the levels of δ-aminolevulinate synthetase which is the rate-limiting enzyme in heme formation.

The compounds tested were 19-noretiocholanolone (A) and its 3-decanoate (B), and 3β-hydroxy-5β-estrane-17-one (C) and its decanoate (D). All compounds were found to be non-pyrogenic.

The results are shown in the following table:

Table I

| Induction of Porphyrin Synthesis by Steroids in Cultured Chick Embryo Liver Cells* | | |
|---|---|---|
| Treatment | No. of Samples and Dose | Protoporphyrin found (pmol/mg protein, 20 hr) |
| Steroid A | 4 – 2μg/ml | $736.0 \pm 27.6$ |
| Steroid A | 4 – 10μg/ml | $814.8 \pm 40.7$ |
| Steroid B | 4 – 2μg/ml | $341.1 \pm 32.0$ |
| Steroid B | 4 – 10μg/ml | $434.5 \pm 45.9$ |
| Steroid C | 4 – 2μg/ml | $647.6 \pm 87.1$ |
| Steroid C | 4 – 10μg/ml | $751.4 \pm 103.4$ |
| Steroid D | 4 – 2μg/ml | Approx. ½ the |

Table I-continued

Induction of Porphyrin Synthesis by Steroids in Cultured Chick Embryo Liver Cells*

| Treatment | No. of Samples and Dose | Protoporphyrin found (pmol/ mg protein, 20 hr) |
|---|---|---|
| Steroid D | 4 – 10μg/ml | values for C |

What is claimed is:

1. Method for the stimulation of erythropoiesis in humans and other warm-blooded animals in need of such therapy which acomprises administering an amount effective to produce such stimulation of a compound selected from the group consisting of 3β-hydroxy-5β-estrane-17-one, and the 3-esters thereof of inorganic acids and of organic carboxylic acids having 3 to 18 carbon atoms, and the 3-ethers thereof in which the ether group is selected from the group consisting of methoxy, ethoxy, propoxy, benzyloxy and phenylethoxy.

2. The method of claim 1 in which said compound is administered parenterally.

3. The method of claim 1 in which said compound is 3β-hydroxy-5β-estrane-17-one.

4. The method of claim 1 in which said compound is the 3-decanoate ester of 3β-hydroxy-5β-estrane-17-one.

5. A pharmaceutical preparation in unit dosage form adapted for parenteral administration for the stimulation of erythropoiesis in humans and other warm-blooded animals, containing as its active ingredient an effective amount within the range from about 5 to about 500 mg. per dosage unit of a compound selected from the group consisting of 3β-hydroxy-5β-estrane-17-one, and the 3-esters thereof of inorganic acids and of organic carboxylic acids having 3 to 18 carbon atoms, and the 3-ethers thereof in which the ether group is selected from the group consisting of methoxy, ethoxy, proposy, benzyloxy and phenylethoxy.

6. The preparation of claim 5 in which said compound is 3β-hydroxy-5β-estrane-17-one.

7. The preparation of claim 5 in which said compound is the 3-decanoate ester of 3β-hydroxy-5β-estrane-17-one.

* * * * *